United States Patent [19]

Steer et al.

[11] Patent Number: 4,770,445
[45] Date of Patent: Sep. 13, 1988

[54] TUBE COUPLING
[75] Inventors: Peter L. Steer; John V. Edwards, both of East Grinstead, United Kingdom
[73] Assignee: E. R. Squibb & Sons, Inc., Princeton, N.J.
[21] Appl. No.: 599,132
[22] Filed: Apr. 11, 1984

Related U.S. Application Data

[63] Continuation of Ser. No. 336,479, Dec. 31, 1981, abandoned.

[30] Foreign Application Priority Data

Jan. 15, 1981 [GB] United Kingdom ................. 8101156
Jun. 30, 1981 [GB] United Kingdom ................. 8120083

[51] Int. Cl.⁴ ............................................. F16L 37/12
[52] U.S. Cl. ................................... 285/110; 285/319; 285/921
[58] Field of Search ............... 285/319, DIG. 22, 423, 285/110, 260 (U.S. only)

[56] References Cited

U.S. PATENT DOCUMENTS

| 921,691 | 5/1909 | Friday | 285/319 X |
|---|---|---|---|
| 1,043,683 | 11/1912 | Fieser . | |
| 1,366,634 | 1/1921 | Clark | 285/319 X |
| 1,384,332 | 7/1921 | Mullenux . | |
| 2,235,020 | 3/1941 | Jones . | |
| 3,133,777 | 5/1964 | Anhalt | 339/91 |
| 3,245,703 | 4/1966 | Manly | 285/319 |
| 3,394,954 | 7/1968 | Sarns | 285/319 |
| 3,453,006 | 7/1969 | Levake | 285/110 X |
| 3,515,413 | 6/1970 | Beall | 285/110 X |
| 3,602,009 | 8/1971 | Powell | 285/319 X |
| 3,603,621 | 9/1971 | Parsons | 285/319 |
| 3,667,781 | 6/1972 | Holbrook | 285/45 |
| 4,123,091 | 10/1978 | Cosentino et al. | 285/319 X |

FOREIGN PATENT DOCUMENTS

| 2657215 | 7/1977 | Fed. Rep. of Germany . |
|---|---|---|
| 2805416 | 9/1978 | Fed. Rep. of Germany . |
| 583364 | 12/1946 | United Kingdom . |
| 2157651 | 6/1973 | France . |
| 2399609 | 3/1979 | France . |
| 583364 | 12/1946 | United Kingdom . |
| 641315 | 8/1950 | United Kingdom . |
| 676799 | 8/1952 | United Kingdom . |
| 1050318 | 12/1966 | United Kingdom . |
| 2039652 | 8/1980 | United Kingdom . |

Primary Examiner—Thomas F. Callaghan
Attorney, Agent, or Firm—Lawrence S. Levinson; Stephen B. Davis

[57] ABSTRACT

A tube coupling adapted particularly for medical use includes three parts, namely a female tubular element 52, a male tubular element 50, and an intermediate ring 100 carrying at least one longitudinally extending latching arm 110. The ring is dimensioned to snap-fit into an external annular groove 90 on either the male or female element and the latching arm has an inwardly-extending hook portion 112 which can engage a flange 58 on the female or the male element as the case may be. This engagement holds these two elements together in an axial direction and allows them to rotate freely relative to one another.

8 Claims, 4 Drawing Sheets

TUBE COUPLING

This is a continuation of application Ser. No. 336,479, filed Dec. 31, 1981, now abandoned.

BACKGROUND OF THE INVENTION

Tube couplings are employed in the medical field both in the hospital environment and for in home patient care. Coupling elements are needed, for example, to connect an ostomy bag to a drainage tube, or to connect an incontinence urine collection device to a drainage tube, or to connect a drainage tube to a drainage bag, or a catheter to a drainage tube. Ideally, the coupling should provide a fluid tight seal, should be simple to manipulate so as to provide for rapid connection and disconnection, and should also accomodate movement by the patient.

Various deisgns of tube couplings for medical use have been proposed as note, for example, U.S. Pat. No. 3,394,954 to Sarns, U.S. Pat. No. 3,245,703 to Manly, and U.S. Pat. No. 3,667,781 to Holbrook. However, for the most part, such prior designs have been difficult to manipulate and have precluded rotation between coupling parts in order to maintain a fluid tight seal.

SUMMARY OF THE INVENTION

According to the invention, there is provided a tube coupling of synthetic plastics material comprising three parts, namely a female tubular element, a male tubular element capable of rotating freely when engaged within the female element, and an intermediate ring carrying at least one longitudinally extending latching arm. The ring is dimensioned to snap-fit into an external annular groove on either the male or female element and the latching arm has an inwardly-extending hook portion which can engage a flange on the female or the male element in order to hold these elements together. The latching arm is deformable by finger pressure in order to bring its hook out of engagement with the flange.

In a preferred embodiment of the invention, the annular groove is on the female element and the flange is on the male element. According to an advantageous feature of the invention, the female element includes an internal deflectible sealing-skirt which engages the outer surface of the male element when the elements are coupled together.

DETAILED DESCRIPTION OF THE INVENTION

Figure 1:
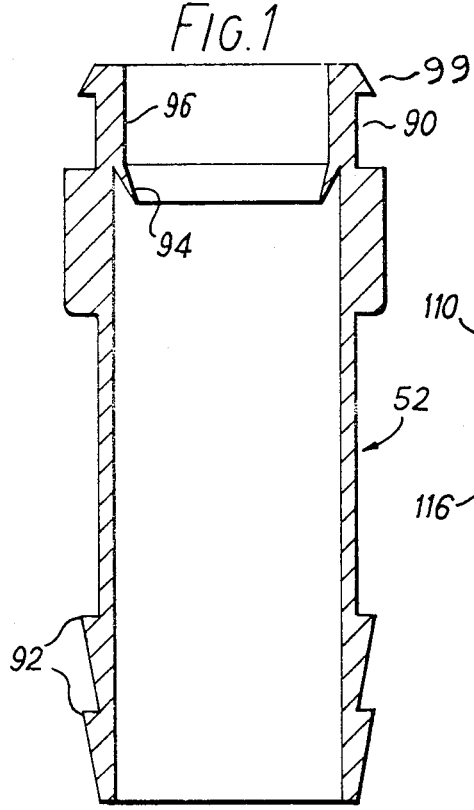
FIG. 1 is an axial cross-section of a female coupling element for use in the invention.
Figure 2:
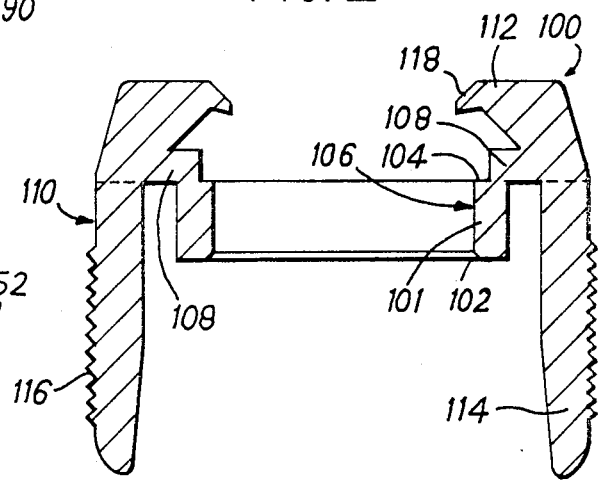
FIG. 2 is an intermediate ring.
Figure 3:
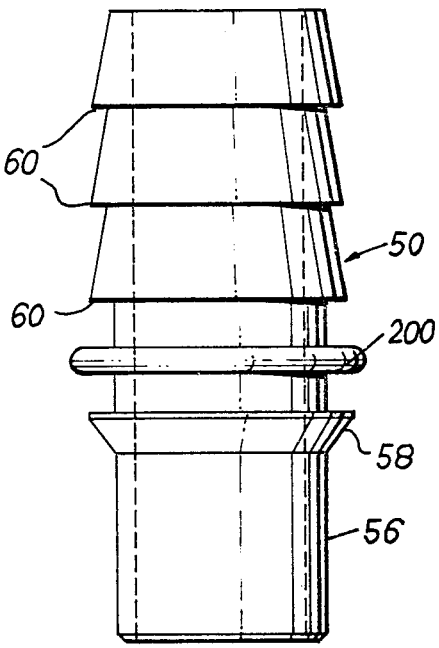
FIG. 3 is an axial cross-section of a male coupling element complementary to the element shown in FIG. 1.
Figure 4:
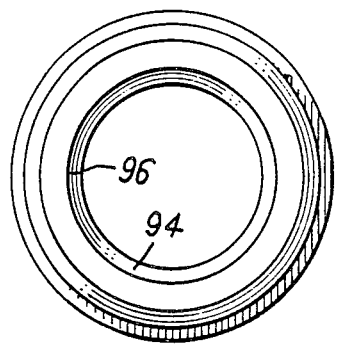
FIG. 4 is an end view of the female element shown in FIG. 1.
Figure 8:
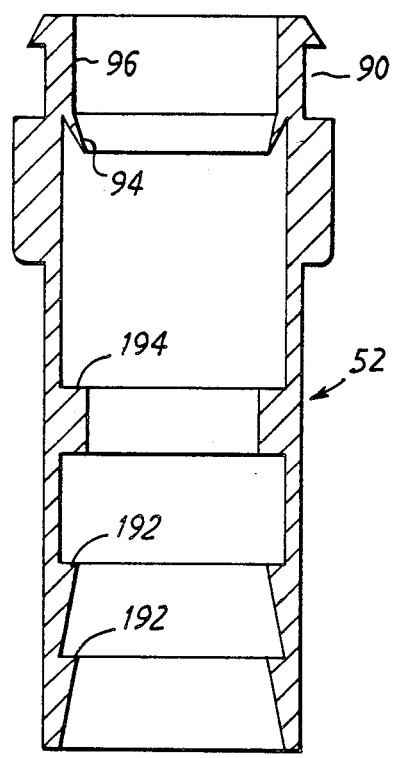
FIG. 8 is a view similar to FIG. 1 of an alternative embodiment of a female coupling element of the invention.
Figure 9:
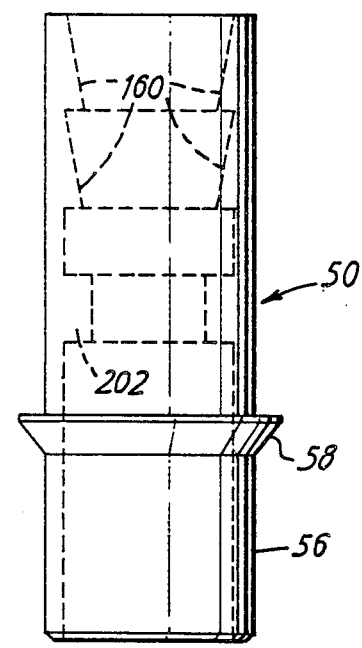
FIG. 9 is a view similar to FIG. 3 of an alternative embodiment of a male coupling element of the invention.

The coupling illustrated in FIGS. 1–6 consists of a male element 50, a female element 52 and an intermediate ring 100. The male element has a tubular body of which one end forms a spigot 56 for insertion in the female element 52. A rim 58 extends radially outwardly around the periphery of the spigot 56. One or more ridges 60, which are optional and may be omitted in certain designs of coupling, are provided on the exterior of the body to facilitate a push fit insertion of the male element in the open end of a plastics tube which is to be connected by the coupling to another tube or an item of equipment. A second rim or flange 200 acts as an end stop to the end of the plastics tube when the tube is pushed on the male element 50 over the ridges 60. Whereas FIGS. 1 and 3 show an arrangement wherein the plastics tubes are pushed over the outside of the male and female coupling elements respectively, it is a perfectly feasible arrangement that the tubes should be fitted inside the cylindrical portions of the coupling elements. Such an arrangement is shown in FIGS. 8 and 9. The female element 52 is shown in FIGS. 1 and 4 and has a hollow body which receives the spigot 56. The spigot 56 can freely rotate within the element 52 when the parts are engaged. Integral with the body are two peripheral ridges 92 which co-operate with the interior wall of a tube or a cylindrical recess to which the female coupling element is to be attached. The element 52 also has a channel-section external peripheral recess or groove 90.

The surface 99 on the element 52 is chamfered so that the ring 101 can be pushed on to the element 52 and snap-fitted into the groove 90.

In the illustrated coupling, good sealing is achieved by the use of an annular deflectible skirt 94, integral with the body, which extends downwardly and slightly inwardly from a narrower bore portion 96 on the female coupling element 52. FIG. 3 illustrates a male coupling element 50 which has a cylindrical spigot 56 chamfered at one end. When the two elements are joined, the spigot is pushed into the female element 52 and forces the skirt 94 slightly outwardly. As an example, the O.D. of the spigot 56 may be 0.335 inch, the I.D. of the narrow bore cylindrical portion 96 of the female element 52 may be 0.340 inch, and the minimum I.D. of the skirt 94 may be 0.330 inch. The male and female elements may be molded from polypropylene. Other polyolefins, nylons, and polyvinyl chloride are also suitable but polypropylene is preferred. It is preferred that the element 52 and skirt 94 should be of a synthetic plastics material having a Shore hardness in the range 65 to 95.

Figure 5:
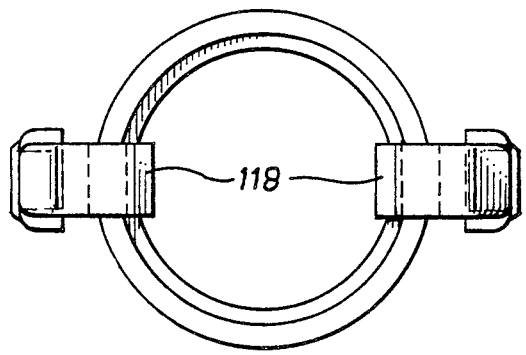
FIG. 5 is an end view of the intermediate ring.
Figure 6:
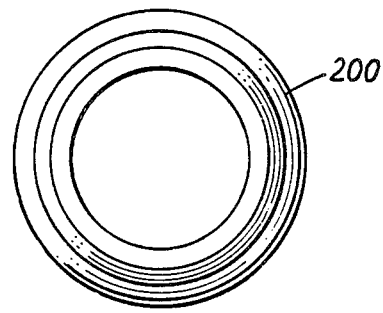
FIG. 6 is an end view of the male element shown in FIG. 3.

The intermediate ring 100 shown in FIGS. 2 and 5 has a ring portion 101 substantially in the shape of a hollow cylinder with its lower inner edge 45° chamfered as seen at 102. The upper portion has a step 104 and the axial length of the inner surface 106 is arranged to be equal to or very slightly less than the axial extent of the recess 90 in the external surface of the female element. At two points diametrically opposite to each other, the ring 101 is integral with two outwardly extending lugs 108 which join respectively latching arms 110 to the ring 100. Each latching arm 110 has a forward inwardly-extending hook portion 112 and a rearward lever arm portion 114. The latter may be knurled on its outer surface as seen at 116. The latching arms 110 are integral with the lugs 108 and the ring 101. The hook portions 112 are located to spring over the rim 58 (FIGS. 3 and 6) when the male and female coupling elements are pushed together. For this purpose each hook portion has a slanting surface 118. The intermediate ring is made by a single molding operation from a synthetic plastics material (e.g., polypropylene) having an appropriate resilience, flexibility and strength. In use, to detach the male coupling element from the intermediate ring and hence from the female element, the lever arm portions 114 of the latching arms are pushed towards each other (e.g., by finger and thumb pressure) so causing the hook portions 112 to more a short distance upwardly and outwardly so releasing the rim 58.

It will be seen that connection of the tube coupling illustrated herein is very simply done by a mere push in an axial direction. Disconnection is also very simple, one merely grips the ring 100 and squeezes the latching arms together, and pulls the element 50 axially out of the element 52. The ring 100 of course remains on the element 52, free to rotate thereon.

The peripheral ridges 60 and 92 are not essential and may be omitted. In this case reliance is placed on the friction between the cylindrical outer surfaces of the female and male elements and the interior of a tube (or other item of equipment) to which it is connected, to hold the female and male elements in place.

In an alternative embodiment of the invention, the deflectible sealing skirt need not be integral with the female coupling element. It could be a separate plastics member, for example made by injection molding, which could be force-fitted into the female element or secured therein by adhesive.

FIGS. 8 and 9 illustrate an alternative arrangement for connecting plastics tubing to the male and female coupling elements. Instead of being pushed on over the substantially cylindrical portions of the elements, the plastics tubes are pushed into said elements. As seen in FIG. 8, the female element 52 has internal ridges 192 which will bite into the outer cylindrical surface of the tube, and an internal rim 194 which serves as an end stop for the tube. As seen in FIG. 9, the male element 50 has internal ridges 160 which likewise hold the tube in place and an internal rim 202 which serves as an end stop. In other respects the female and male coupling elements are as described in connection with FIGS. 1 and 3. It would be possible if desired to use a female coupling element having its tube internally secured (as per FIG. 8) in conjunction with a male coupling element having its tube pushed over (as per FIG. 3). Likewise if desired it would be possible to use a female coupling element according to FIG. 1 with a male element according to FIG. 9 if it was necessary to couple two tubes of different diameter.

Figure 7:
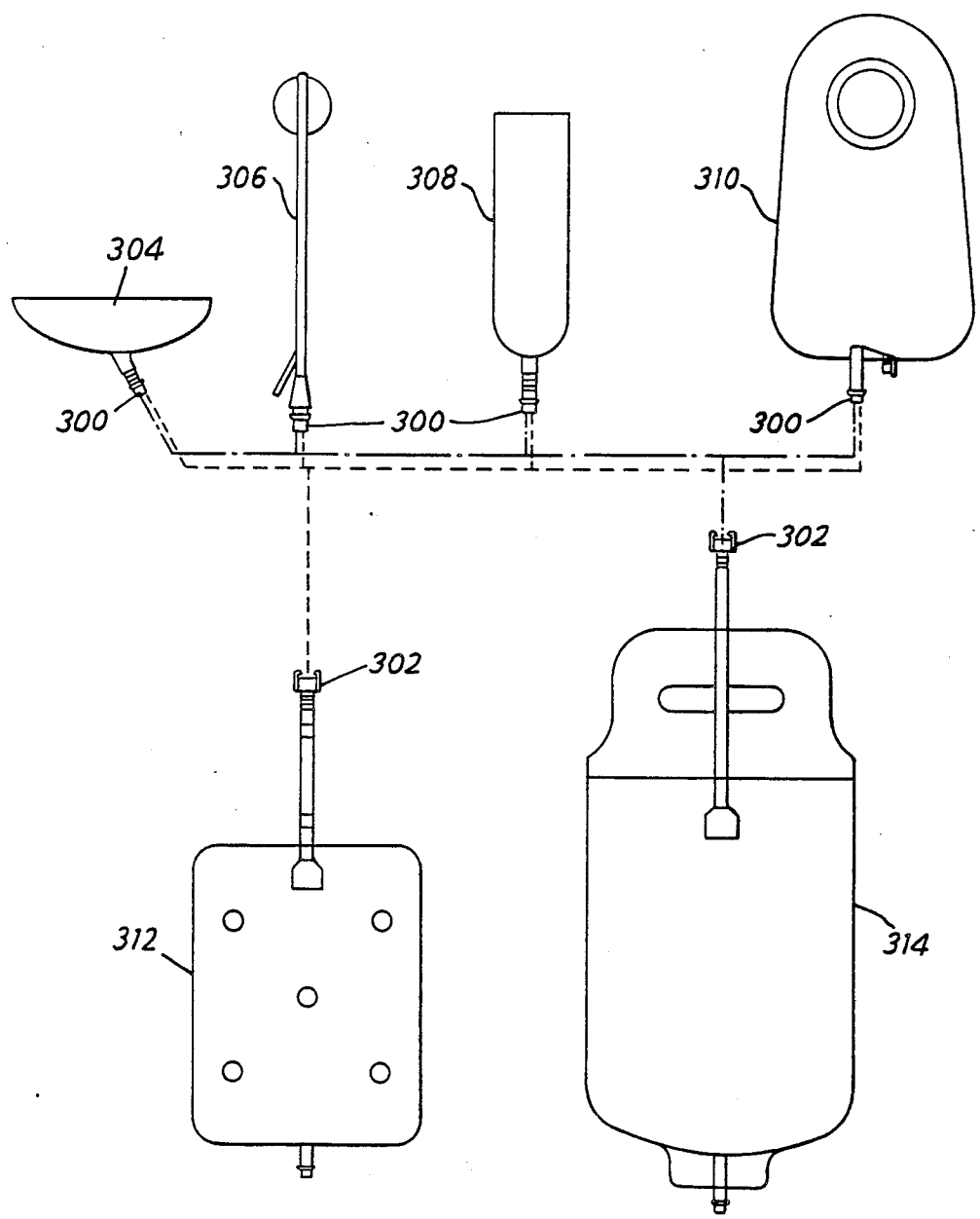
FIG. 7 is illustrates a number of possible uses in the medical field of a coupling according to the invention.

FIG. 7 diagrammatically illustrates a number of possible uses in the medical-surgical field for a coupling according to the invention. The coupling elements are shown as elements 300 and 302. One coupling element 300 may be used on a female incontinence device 304, a catheter 306, a male incontinence device 308, or on an ostomy bag 310. The other coupling element 302 may be used on a leg bag 312 or on a night drainage bag 314. Other uses will occur to one skilled in the art.

Although not illustrated in the drawings, according to another feature of this invention, a breather hole may be provided in the cylindrical wall of female coupling element just above the uppermost (as seen in FIG. 1) ridge 92. This hole would be covered by a patch of a microporous material which is permeable to air but is impermeable to liquids. In this way, air can be allowed to enter a drainage tube reducing the chance of a build-up of negative pressure therein due to the flow of liquid. A suitable microporous material is an adhesive patch of tape commercially available under the trade name Micropore. Alternatively, the breather hole covered by a patch of microporous material could be provided in the male coupling element, for example between the lowermost ridge 60 seen in FIG. 3 and the rim 200.

An important advantage of the coupling construction according to the invention is that the intermediate ring is free to rotate relative to the female element and/or relative to the male element. Hence, whatever the constraints upon the rotational positions of the male and female elements, and such constraints are normally imposed by the location or construction of other pieces of equipment connected to the far ends of the tubes bearing the male and female elements, it is always possible by rotating the intermediate ring to position the latching arms where they can conveniently be squeezed between finger and thumb. While at first sight this may appear to be a relatively minor feature, it is one of considerable practical importance because these couplings are normally connected and disconnected by nurses who often have only one hand available for the task and who will have to make hundreds of such connections and disconnections in a working day. Moreover, the provision of free rotation between male and female coupling elements allows one of the coupled tubes to rotate relative to the other. This is of importance in avoiding kinking and when one tube is part of or directly connected to a urine bag, undesired deformation or dislodgement of the bag from its holder or hanger is less likely to occur.

What is claimed is:

1. A tube coupling of synthetic plastics material comprising:
    a hollow tubular shaped female coupling element having an upper end adapted to receive a male coupling member;
    a hollow tubular shaped male coupling element having a lower end spigot portion dimensioned to fit with said upper end of said female coupling element and capable of rotating freely when engaged within said female element;
    and an intermediate ring being dimensioned to snap-fit into an annular groove on the external tubular surface of either said male or said female coupling element, said intermediate ring being freely rotatable within said annular groove independent of said male and female coupling elements even when they are coupled, and an outwardly extending rim located on the external tubular surface of the other coupling element, said intermediate ring carrying at least one longitudinally extending latching arm having an inwardly extending hook portion which can engage said rim in order to hold the two coupling elements together, said latching arm being deformable by finger pressure in order to bring said hook out of engagement with said rim.

2. A tube coupling according to claim 1 wherein said annular groove is on the female coupling element and said rim is on the male coupling element.

3. A tube coupling according to claim 2 wherein the upper end of said female coupling element includes an internal deflectible sealing skirt which in use is slightly outwardly deformed by insertion of the spigot portion of said male coupling element.

4. A tube coupling according to claim 3 wherein one or more ridges are located on the external surface of said female coupling element near its lower end to facilitate a push fit of said female element into an open ended tube or item of equipment.

5. A tube coupling according to claim 3 wherein one or more ridges are located on the external surface of said male coupling element near its upper end and an outwardly extending flange is located on the external surface of said male coupling element above said rim to facilitate a push fit of an open ended tube onto said male coupling element with said flange acting as a stop for said tube.

6. A tube coupling according to claim 1 wherein said annular groove is on the male coupling element and said rim is on the female coupling element.

7. A tube coupling according to claim 6 wherein the upper end of said female coupling element includes an internal deflectible sealing skirt which in use is slightly outwardly deformed by insertion of the spigot portion of said male coupling element.

8. A tube coupling of synthetics plastic material comprising:

a hollow tubular shaped female coupling element having an internal deflectable sealing skirt at its upper end and a substantially constant internal diameter along its length above said deflectable sealing skirt, said constant internal diameter dimensioned so that said upper end of said female element can receive a male coupling member, one or more ridges located on the external surface of said female element near its lower end to facilitate a push fit of said element into an open ended tube or item of equipment, and an annular groove on the external tubular surface of said female coupling element;

a hollow tubular shaped male coupling element having a lower end spigot portion with an external diameter dimensioned to fit within the substantially constant internal diameter of said upper end of said female coupling element and which slightly outwardly deforms said deflectable sealing skirt upon insertion of said spigot portion into said upper end female coupling element, said male coupling element capable of rotating freely when engaged within said female element, an outwardly extending rim located on the external tubular portion of said male coupling element, and one or more ridges located on the external tubular surface of said male coupling element near its upper end and an outwardly extending flange located on the external tubular surface of said male coupling element above said rim to facilitate a push fit of an open ended tube onto said male coupling element with said flange acting as a stop for said tube; and an intermediate ring being dimensioned to snap-fit into said annular groove on the external tubular surface of said female coupling element, said intermediate ring being freely rotatable within said annular groove independent of said male and female coupling elements even when they are coupled, said intermediate ring carrying at least one longitudinally extending latching arm having an inwardly extending hook portion which can engage said rim on the external surface of said male coupling element in order to hold the two coupling elements together, said latching arm being deformable by finger pressure in order to bring said hook out of engagement with said rim.

* * * * *